United States Patent [19]

Leight

[11] 3,970,082

[45] *July 20, 1976

[54] HARD HAT EAR PROTECTOR

[76] Inventor: Howard S. Leight, 16027 Northfield St., Pacific Palisades, Calif. 90272

[ * ] Notice: The portion of the term of this patent subsequent to Oct. 15, 1991, has been disclaimed.

[22] Filed: Sept. 3, 1974

[21] Appl. No.: 502,308

Related U.S. Application Data

[63] Continuation-in-part of Ser. No. 346,747, April 2, 1973, Pat. No. 3,841,326.

[52] U.S. Cl. .................................... 128/152; 2/423
[51] Int. Cl.² ......................................... A61F 11/00
[58] Field of Search .................. 128/152, 151, 132; 2/3 R, 185, 3 C, 209

[56] References Cited
UNITED STATES PATENTS

| | | | |
|---|---|---|---|
| 997,673 | 7/1911 | Hegge | 128/152 |
| 3,016,054 | 1/1962 | Rosenblatt | 128/152 |
| 3,461,463 | 8/1969 | Beguin | 2/209 X |

Primary Examiner—Robert W. Michell
Assistant Examiner—Henry J. Recla
Attorney, Agent, or Firm—Lindenberg, Freilich, Wasserman, Rosen & Fernandez

[57] ABSTRACT

An ear protector assembly which can be mounted on a protective helmet, including a mount which can be attached to the side of the helmet, a linkage pivotally connected to the mount, and an earplug mounted on an end of the linkage. The linkage includes a pair of pivotally mounted bars that enable adjustment of the earplug position into alignment with the ear canal of the wearer, while resisting outward deflection so the earplug can be pressed against the ear canal. The linkage can be resiliently deflected outwardly so the earplug can move around the rim of the helmet and rest upon the rim for stowage out of the way of the wearer.

2 Claims, 7 Drawing Figures

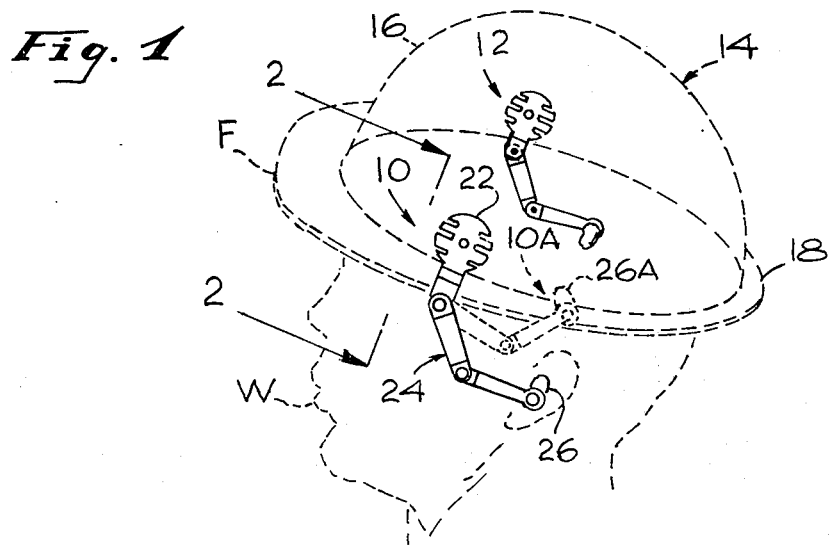
Fig. 1
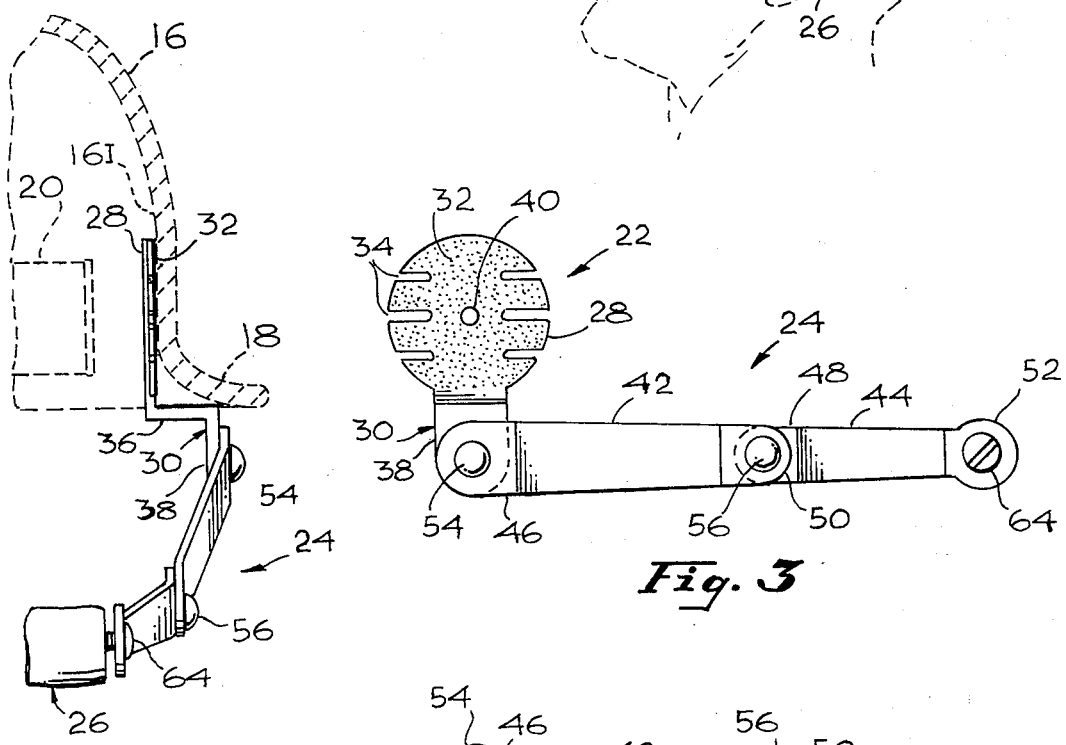
Fig. 2
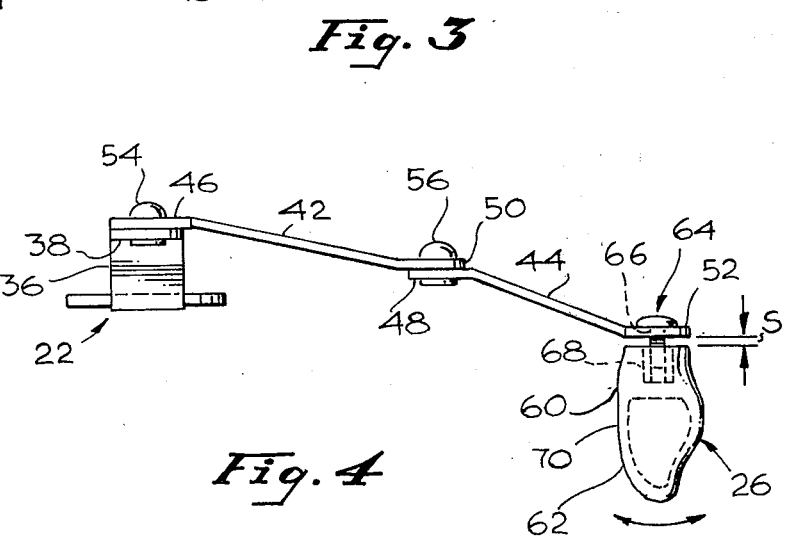
Fig. 3
Fig. 4

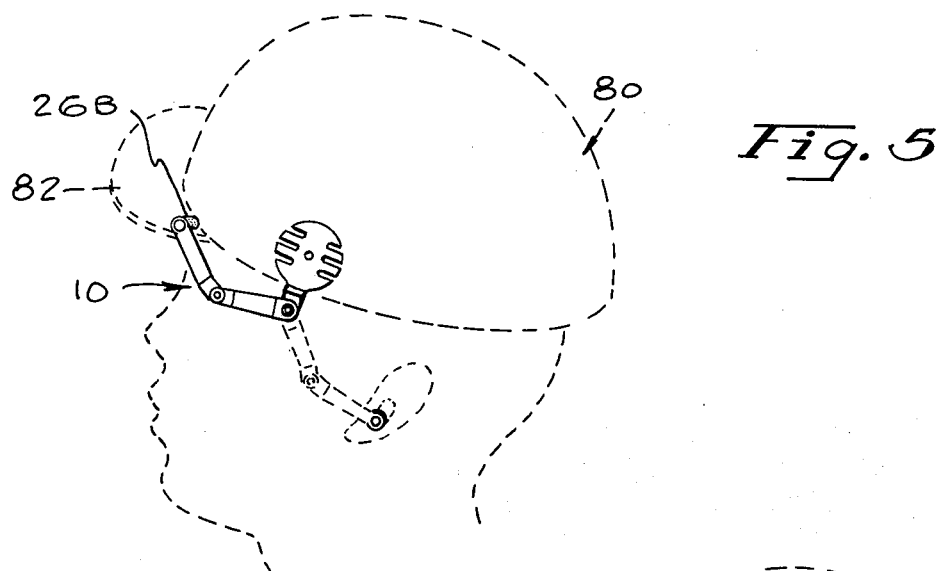
Fig. 5
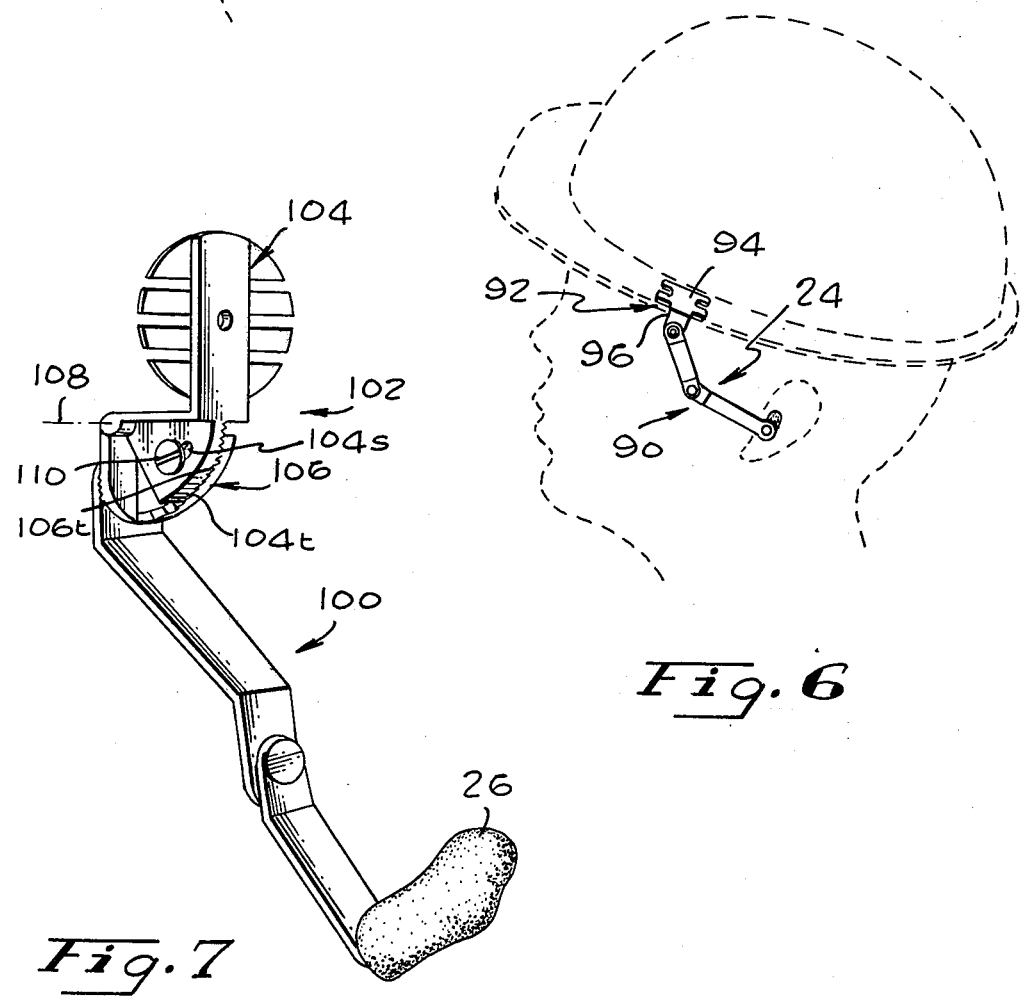
Fig. 6
Fig. 7

HARD HAT EAR PROTECTOR

CROSS-REFERENCE TO RELATED APPLICATON

This is a continuation in part of patent application Ser. No. 346,747 filed Apr. 2, 1973 now Pat. No. 3,841,326.

BACKGROUND OF THE INVENTION

Workmen who must wear protective helmets or hard hats to protect against falling objects and the like, must occasionally work around very noisy machinery. Ear protectors are available with an earplug-holding band that extends under the chin or behind the head, to enable wearing while the workman also wears a helmet. However, the necessity to carry and store a separate ear protector, in addition to the protective helmet, is inconvenient and annoying to workmen, and therefore the ear protectors are often unavailable when the need for them arises.

SUMMARY OF THE INVENTION

In accordance with one embodiment of the present invention, an ear protector assembly is provided which can be attached to an ordinary protective helmet, which can be easily adjusted to comfortably and effectively fit the wearer after he has put on the helmet, and which can be easily stowed on the helmet without dangling or the like when ear protection is not needed. The ear protector assembly includes a mount which is attached facewise to the inner surface of the helmet and which has a tab extending below the rim of the helmet. A two-bar linkage has one end pivotally connected to the tab of the mount and an opposite end which carries an earplug. The linkage can be pivoted between a use position wherein the earplug is at the wearer's ear canal, and a stowage position wherein the earplug rests on the rim of the helmet. The linkage applies inward force so that the earplug is pressed against the ear canal in the use position and is retained on top of the rim of the helmet in the stowage position, and yet the earplug can be deflected outwardly to clear the rim in movement between the use and stowage positions. A workman can readily attach a pair of ear protector assemblies to the opposite sides of his helmet so that they are always available. The earplugs may be normally kept in the stowage position, but a workman can readily use them by pushing the earplugs outwardly to clear the rim and then pivoting the linkage so that the earplugs lie against his ear canals.

The novel features that are considered characteristic of this invention are set forth with particularity in the appended claims. The invention will best be understood from the following description when read in connection with the accompanying drawings.

BRIEF DESCRIPTION OF THE DRAWINGS

FIG. 1 is a perspective view of ear protector assemblies constructed in accordance with the present invention on a protective helmet;

FIG. 2 is a view taken on the line 2—2 of FIG. 1;

FIG. 3 is a front elevation view of the ear protector assembly of FIG. 1;

FIG. 4 is a bottom view of the ear protector assembly of FIG. 3;

FIG. 5 is a perspective view of an ear protector assembly of FIG. 1 on another type of helmet, showing how the earplug can be stored on a visor portion of a rim;

FIG. 6 is a perspective view of an ear protector assembly constructed in accordance with another embodiment of the invention, for mounting on the rim of a helmet; and FIG. 7 is a perspective view of an ear protector assembly constructed in accordance with still another embodiment of the invention.

DESCRIPTION OF THE PREFERRED EMBODIMENT

FIG. 1 illustrates a pair of ear protector assemblies 10, 12 that are mounted on a hard hat or protective helmet 14. The helmet 14 includes a largely hemispherical shell 16, a rim 18 extending around the bottom of the shell, and a helmet liner 20 (FIG. 2) which is attached to the shell 16. The shell 16 and rim 18 are constructed of a hard material, such as steel or a rigid plastic, while the liner 20 is constructed of a soft plastic or other soft material. The helmet is worn in a predetermined orientation, with a front helmet portion F at the front of the wearer's head. The ear protector assemblies 10, 12 are attachments that can be readily mounted on either side of the helmet to provide conveniently available ear protection. Each ear protector assembly includes a mount 22 mounted on the shell 16, an earplug holder 24 in the form of a two bar linkage, and an earplug 26 mounted on the linkage. The linkage of each ear protector assembly, such as assembly 10, can be moved between a use position, illustrated in solid lines in FIG. 1, wherein the earplug 26 is pressed against the ear canal of the wearer W, and a stowage position illustrated in phantom lines at 10A wherein the earplug at 26A rests upon the rim 18 of the helmet. A workman may normally store and wear the helmet with the ear protector assemblies in the stowage position wherein they are out of the way of his head. However, the ear protectors are always conveniently available for movement into the use position when the ambient noise rises to a a high level.

As also illustrated in FIGS. 2–4, the mount 22 includes a round sheet-like member 28 designed for attachment facewise to the inner surface 16I of the helmet shell, and a tab 30 that extends downwardly from the flat member 28 and which pivotally supports the linkage 24. The flat member 28 has a pressure sensitive adhesive 32 on one face thereof which lies against the inner surface of the helmet to permit rapid mounting thereon. The member 28 has several laterally-extending slots 34 on each side to permit a degree of flexibility in twisting about a vertical axis to facilitate inward and outward movement of the earplugs towards and away from the wearer, and to facilitate secure attachment to the helmet surface even though the helmet is curved. The tab 30 includes a horizontally-extending upper ledge portion 36 that bears against the rim 18 of the helmet and a lower tab portion 38 on which the linkage 24 is mounted. In order to provide an opportunity for more secure mounting, a hole 40 is formed through the flat portion to receive a screw, so that a workman can drill a corresponding hole at each side of his helmet and fasten the mount to the inside of the helmet with a screw and nut.

The linkage 24 includes two bars 42, 44 that are pivotally joined together and to the mount. The inner bar 42 has an inner end 46 pivotally mounted on the tab portion 38. The outer bar 44 has an inner end 48 pivotally joined to the outer end 50 of the bar 42 and has an outer end 52 that supports the earplug 26. As illustrated in FIG. 4, each bar 42, 44 has a middle portion that extends at an angle towards the wearer. Accordingly, the mount 22 is spaced from the wearer's ear but the earplug 26 lies close to the wearer's ear and can nest against the ear canal of the wearer. A pair of pivot joint members 54, 56 that pivotally connect the bar 42 to the tab 38 and pivotally connect the two bars together, form low enough friction joints to permit a workman to readily adjust the linkage so that the earplug fits against his ear. The two-bar linkage permits the earplug to reach the ear for a wide range of mounting locations on the helmet.

The pivots 54, 56 are tight enough so as to resist wobbling movement, and the bars 42, 44 are flexible and the mount 22 adds additional flexibility to permit resilient movement of the earplugs away from a position against the wearer's head. Thus, while the ear protector assembly normally urges the tip of the earplug 26 against the ear canal to firmly seat it thereon, a workman can readily move out the earplug so it can clear the rim 18 of his helmet while he lifts the earplug onto the rim. When the earplugs 26 rest on the helmet rim 18, they are out of the way of the wearer so that they will not swing at the side of his head. The earplug 26 is unlikely to accidentally fall off the rim because it is being pressed inwardly towards the helmet by the resilient linkage and mount. Of course, a workman can readily move the apparatus to a use position by pulling out the earplug 26 or outer link bar 44 so the earplug clears the rim 18 and can be moved down to a position at the ear canal.

The earplug 26 is constructed of a soft flexible material with a solid base 60 and a hollow tip 62. The base is attached to the end 52 of the linkage bar 44 by a screw fastener 64 that is threaded into a hole 66 in the bar end and into an insert 68 in the earplug. The earplug is mounted with a spacing s of the earplug base 60 from the link bar end 52, which permits a limited flexible deflection of the earplug to properly enter the wearer's ear. This is especially important because the earplug 26 is flattened along one side 70 to fit along the tragus of the ear, and the flexibility of earplug mounting permits the earplug to lie flat thereagainst.

An ear protector assembly such as 10 can be used with a variety of helmet types. FIG. 5 illustrates the assembly 10 mounted on a helmet 80 which has a rim 82 only at the front thereof which forms a visor. The ear protector assembly can be stored, as illustrated in FIG. 5 by pivoting it forwardly until the earplug at 26B lies over the rim 82 at the front of the helmet.

An ear protector assembly can be constructed to mount on the rim of the helmet, as shown for the assembly 90 of FIG. 6. This is accomplished by modifying the mount as to the configuration shown at 92, wherein a flat member 94 with adhesive on its upper surface has a small enough length to fit on the rim. The linkage 24 is the same as that of FIGS. 1–5, and is mounted on a downwardly depending tab 96 similar to the tab 30 of FIG. 3. Of course, for a helmet with only a front rim portion or visor, the linkage 24 can be made long enough to allow mounting on the front rim portion.

FIG. 7 illustrates a modified ear protector assembly 100 which is similar to that of FIGS. 1–5, but which has an adjustable mount 102 for permitting adjustment of the force with which the earplug 26 presses against the ear. The mount 102 has a pair of mount members 104, 106 pivotally joined along an axis of pivoting 108 and including a clamping screw 110 for holding the mount members at any relative orientation within a range of about 30° of pivoting. The two mount members having interfitting teeth 104t, 106t that prevent slippage. One of the mount members 104 has a slot 104s and the other has a threaded screw-receiving hole into which the screw fits. The earplug holder 24 is pivotally mounted on the mount member 106, while the other member 104 is fixed to the helmet. The inner end of the holder has small ratchet teeth 24r that engage corresponding teeth 106r on the mount member 106 to prevent free pivoting.

Thus, the invention provides an ear protector assembly usable with a protective helmet so that protection from loud noises is available when the helmet is worn. The assembly is constructed to facilitate mounting on the helmet in a secure manner, and to permit adjustment of the earplug position to fit the wearer while providing an inward bias for securely holding the earplug against the ear canal of the wearer. This is accomplished by providing a linkage with at least one bar, and which can provide an inward force to hold the earplug against outward deflection until a large deflecting force is applied. The assembly also permits secure stowage when the earplug is not being worn in the ear, by permitting an orientation wherein the earplug rests over the rim of the protective helmet and is biased inwardly thereagainst so that it does not accidentally fall down to dangle in the way of the wearer. Either the earplug 26 or a part of the linkage 24 may actually contact the helmet rim in such a stowage position.

Although particular embodiments of the invention have been described and illustrated herein, it is recognized that modifications and variations may readily occur to those skilled in the art and consequently it is intended that the claims be interpreted to cover such modifications and equivalents.

The embodiments of the invention in which an exclusive property or privilege is claimed are defined as follows:

1. Protective apparatus for mounting on a protective helmet that has a rim comprising:
 a mount which is mountable on a protective helmet;
 link means having a first end pivotally connected to the mount and a second end;
 an earplug; and
 means for mounting said earplug on said second end of said link means;
 said mount including a first member having means for fixing it to a helmet and a second member which is pivotally connected to said link means, said first and second members being pivotally joined to permit pivoting about a predetermined axis, and said first and second members having teeth spaced about said axis with at least one tooth on each member engaged with a tooth on another member, to maintain said members at any one of a plurality of relative angular orientations.

2. Protective apparatus comprising:
 a helmet with a rim, said helmet having opposite sides;
 a pair of mounts mounted on either side of the helmet on the underside of the rim;
 a pair of earplug holders, each having one end pivotally attached to a corresponding mount and a second end; and a pair of inwardly protruding earplugs, each mounted on the second end of a corresponding earplug holder;

each earplug holder including means for permitting movement of the earplug thereon up and down between a use position wherein the earplug lies below the rim and against the ear, and a stowage position wherein the earplug lies above the rim and on the outside of the helmet so that the earplug is out of the way.

* * * * *